United States Patent
Murphy et al.

(10) Patent No.: US 6,183,126 B1
(45) Date of Patent: *Feb. 6, 2001

(54) METHOD FOR NONDESTRUCTIVE/NONCONTACT MICROWAVE DETECTION OF ELECTRICAL AND MAGNETIC PROPERTY DISCONTINUITIES IN MATERIALS

(75) Inventors: John C. Murphy, Clarksville; Robert Osiander; Jane W. Maclachlan Spicer, both of Columbia, all of MD (US)

(73) Assignee: The John Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/886,236

(22) Filed: Jul. 1, 1997

Related U.S. Application Data

(63) Continuation of application No. 08/225,848, filed on Apr. 11, 1994, now abandoned.

(51) Int. Cl.$^7$ .................................................. G01N 25/72
(52) U.S. Cl. .............................................. 374/5; 374/161
(58) Field of Search ........................ 374/4, 5, 7, 161; 324/315, 316, 317, 631–634, 636, 637, 639

(56) References Cited

U.S. PATENT DOCUMENTS

| | | | |
|---|---|---|---|
| 3,942,107 | * | 3/1976 | Gerhard ............................. 324/633 |
| 4,514,680 | * | 4/1985 | Heikkila et al. ..................... 324/631 |
| 4,634,963 | * | 1/1987 | Lunden ............................... 324/633 |
| 4,679,946 | * | 7/1987 | Rosencwaig et al. ................... 374/5 |
| 4,707,652 | * | 11/1987 | Lowitz ............................... 324/631 |
| 4,996,426 | * | 2/1991 | Cielo et al. ........................... 374/5 |
| 5,123,144 | * | 6/1992 | Demuth et al. ........................ 374/5 |
| 5,124,662 | * | 6/1992 | Downing et al. ..................... 324/631 |
| 5,228,776 | * | 7/1993 | Smith et al. ............................ 374/5 |
| 5,239,269 | * | 8/1993 | Martens et al. ...................... 324/633 |
| 5,396,068 | * | 3/1995 | Bethea ................................... 374/5 |

OTHER PUBLICATIONS

B. Hillemeier, "Location of Reinforcement by Induction–Thermography", in Thermosense VII, Proc. SPIE 520, pp. 197–206 (1984).

J.C.Murphy, J.W.Maclachlan and L.C.Aamodt, "Thermal Techniques for Nondestructive Characterization of Layered Structures and Interfaces", Johns Hopkins APL Technical Digest, vol. 9, No. 3, pp. 221–231 (1988).

J.W.Maclachlan Spicer, W.D.Kerns, L.C.Aamodt and J.C.Murphy, "Measurement of Coating Physical Properties and Detection of Coating Disbonds by Time–Resolved Infrared Radiometry", J.Nondestr. Eval., vol. 8, No. 2, pp. 107–120 (1989).

J.W.Maclachlan Spicer, L.C.Aamodt, and J.C.Murphy, "Thermal Nondestructive Characterization of the Integrity of Protective Coatings", Johns Hopkins APL Technical Digest, vol. 11, No. 1–2, pp. 175–179 (1990).

(List continued on next page.)

*Primary Examiner*—Andrew H. Hirshfeld
(74) *Attorney, Agent, or Firm*—Francais A. Cooch

(57) ABSTRACT

Nondestructive/noncontact evaluation of a material for electrical and magnetic property discontinuities, e.g., a dielectric loss or the presence of a conducting contaminant, is accomplished by using microwaves to heat microwave-absorbing regions of the material caused by such discontinuities; monitoring the change in temperature of the material's surface due to the heating of the microwave-absorbing region as a function of time; and detecting the electrical and magnetic property discontinuities, e.g., the dielectric loss or the conducting contaminant, using the change in the material's surface temperature.

29 Claims, 3 Drawing Sheets

OTHER PUBLICATIONS

J.W.Maclachlan Spicer, W.D.Kerns, L.C.Aamodt and J.C.Murphy, "Time–Resolved Infrared Radiometry for Characterization of Structured Materials", in Photo–acoustic and Photothermal Phenomena, J.C.Murphy et al., eds, Springer Series in Optical Science, vol. 62 (Springer–Verlag, Berlin, Heidelberg, 1990) pp. 55–58.

L.C.Aamodt et al., "Analysis of Characteristic Thermal Transit Times for Time–Resolved Radiometry Studies of Multilayered Coatings", J. Appl. Phys., vol. 68, No. 12, pp. 6087–6098 (1990).

J.W.Maclachlan Spicer et al., "Time–Resolved Infrared Radiometry (TRIR) for Characterization of Impact Damage in Composite Materials", in Review of Progress in Quantitative NDE, D.O.Thompson et al., eds., vol. 11 (Plenum Press, 1992), pp. 433–440.

J.W.Maclachlan Spicer et al., "Source Patterning in Time–Resolved Infrared Radiometry (TRIR) of Composite Structures", in Thermosense XIV, J.K.Eklund, ed., Proc. SPIE 1682, pp. 248–257 (1992).

J.W.M.Spicer et al., "Thermal Characterization of Heat Sink Adhesive Systems for Spacecraft Electronics by Time–Resolved Infrared Radiometry", Electronic Packaging, Mar. 1993, vol. 115, pp. 101–105.

J.W.Maclachlan Spicer et al., "Characterization of Hidden Airframe Corrosion by Time–Resolved Infrared Radiometry", Review of Progress in Quantitative NDE, D.O.Thompson et al, eds., vol. 12 (Plenum Press, 1993), pp. 2027–2034.

* cited by examiner

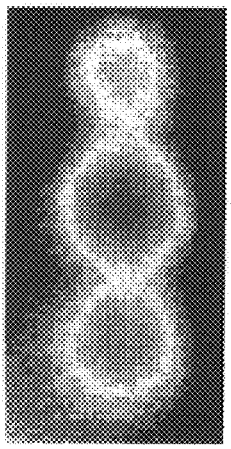 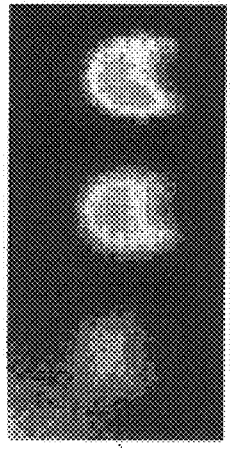 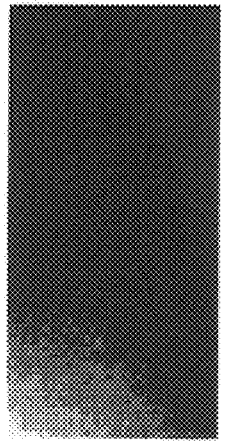
FIG. 3A            FIG. 3B            FIG. 3C
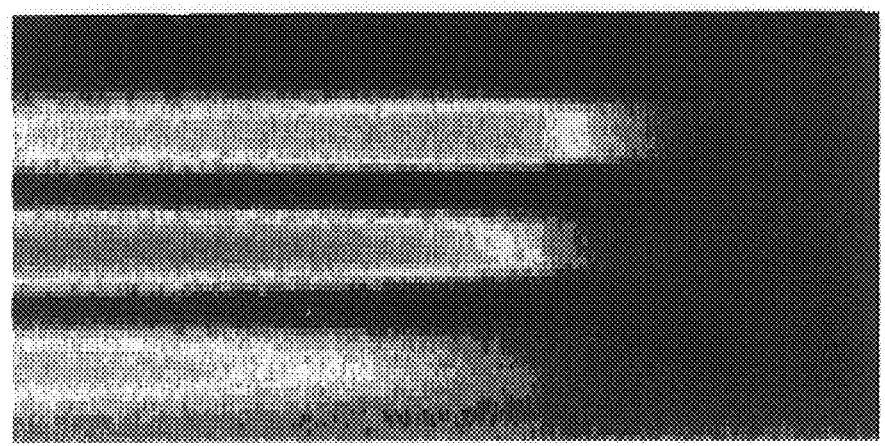
FIG. 3D

METHOD FOR NONDESTRUCTIVE/ NONCONTACT MICROWAVE DETECTION OF ELECTRICAL AND MAGNETIC PROPERTY DISCONTINUITIES IN MATERIALS

This application is a continuation of application Ser. No. 08/225,848, filed Apr. 11, 1994, now abandoned.

STATEMENT OF GOVERNMENTAL INTEREST

The Government has rights in this invention pursuant to Contract No. N00039-91-C0001 awarded by the Department of the Navy.

BACKGROUND OF THE INVENTION

The invention is in the field of thermal wave imaging/sensing and characterization for nondestructive/noncontact evaluation. Specifically, the invention comprises the use of microwave heating with Time Resolved Infrared Radiometry (TRIR) methods.

TRIR is a thermal characterization technique developed for the nondestructive evaluation of layered materials. In TRIR a region close to a sample's surface is heated by a source, e.g., a laser or flashlamp, with a long pulse and the sample's surface temperature is monitored as a function of time through changes in emitted infrared radiation. Specimen features which influence the production or transport of heat cause the surface temperature to change relative to areas without such features. This has allowed subsurface delaminations to be imaged.

An infrared imaging camera allows rapid, quantitative inspection at relatively high spatial resolution. However, the visibility of the subsurface specimen features in the thermal image is determined by the magnitude of the reflected thermal signal which is determined by the depth of the defect and the ratio of the thermal effusivities of region and sample. For example, for subsurface voids filled with water this contrast is small.

SUMMARY OF THE INVENTION

In the method of the invention, a specimen/sample of a material is illuminated/heated with microwaves and then a temperature imaging/sensing means/method, such as an infrared imaging device (e.g., focal plane array), monitors the heating in the specimen due to electrical and/or magnetic property discontinuities, e.g., dielectric loss or the presence of a conducting contaminant.

For optically opaque but microwave transparent materials containing localized absorbing regions the use of a microwave heating source, when compared with conventional laser or flashlamp sources, has distinct advantages. For particular specimen geometries and material properties, the presence of the defect region can be imaged at higher contrast and better spatial resolution than for the surface heating case of TRIR, hence, enhancing the detectability of such defect regions. Since the temperature has only to diffuse to the surface, the characteristic thermal transit times for the measurement are shorter. Moreover, since three-dimensional diffusion acts as a spatial low pass filter and reduces the image resolution of localized thermal features, the shorter path for the thermal signal allows better resolution. Finally, when the region of interest can be selectively heated by specific microwave wavelengths, the image contrast is enhanced.

BRIEF DESCRIPTION OF THE DRAWINGS

FIG. 3, consisting of FIGS. 3(a), 3(b), 3(c) and 3(d), illustrates infrared images of the test sample of FIG. 2 taken (a) before, (b) during and (c) after a 2.7-second microwave pulse, and (d) an 8-second x-time image during a 2.7-second microwave pulse, where the temperature along a single line in FIG. 3(a) is shown as a function of time.

DESCRIPTION OF THE PREFERRED EMBODIMENTS

In the method of the invention, a specimen/sample of a material is illuminated/heated with microwaves and then a temperature imaging/sensing means/method, such as an infrared imaging device (e.g., focal plane array), monitors the heating in the specimen from microwave-absorbing regions due to electrical and/or magnetic property discontinuities, e.g., dielectric loss or the presence of a conducting contaminant.

The use of a microwave source in TRIR provides the ability to heat surface and subsurface microwave-absorbing regions directly, provided the host material is transparent or semi-transparent to microwaves. Thermal diffusion from the heated region to the surface causes a change in the surface temperature of the host and this change can be detected using temperature sensing, e.g., infrared imaging, methods. Furthermore, by varying the frequency of the microwaves, molecular species in the material can be selectively excited.

The invention uses the time-dependence of the temperature distribution to produce images of subsurface microwave absorbing features in the specimen which are much smaller than a microwave wavelength. Comparison with theoretical calculations shows that it is possible to obtain quantitative information about the electromagnetic and thermal properties of the features and their depth in the sample from the time-dependent temperature.

Figure 1:
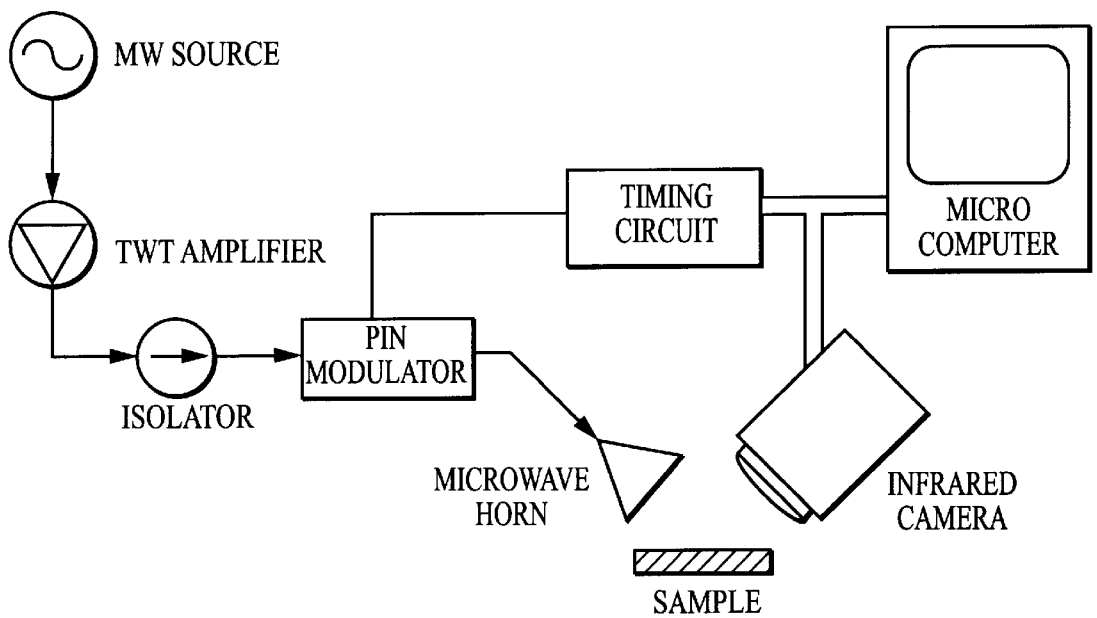
FIG. 1 illustrates a schematic diagram of an example experimental setup to test the method of the invention to detect dielectric loss in a test sample.

FIG. 1 shows a schematic diagram of an example experimental setup used to test the method of the invention to detect dielectric loss. The microwave pulse is generated by an oscillator and then amplified by a traveling wave tube amplifier.

A horn antenna is placed close to the test sample surface at the desired angle, in this example 45°.

Figure 2:
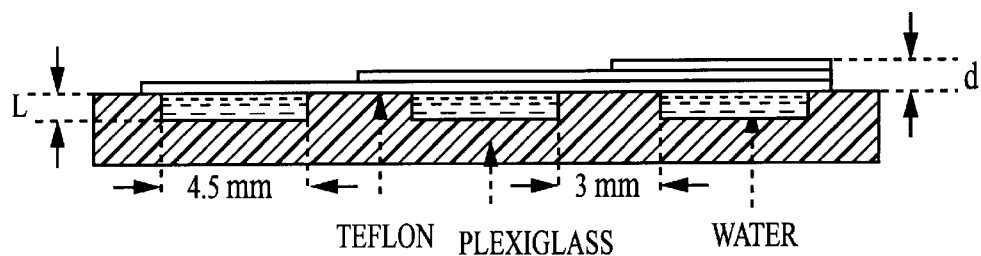
FIG. 2 illustrates a test sample used in the experimental setup of FIG. 1.

The surface temperature of the test sample is monitored in this case by an infrared scanner but the invention, in general, could use any temperature sensing method/device. For example, in addition to the devices already mentioned, the surface temperature could be sensed by monitoring either the variations in the optical reflectivity of the surface of the material or the deflection of a probe beam skimming over the material's surface. The microwave pulse and the scanner frame rate are synchronized and images constructed using a computer. The test sample shown in FIG. 2 is a structured multilayer formed from a Teflon layer of varied thickness, d, a water layer of constant thickness, L, below the Teflon and a Plexiglass backing.

FIG. 3 shows x-y images of the sample taken (a) before, (b) during and (c) after a 2.7 s microwave pulse. The three water layers appear in the images in a temporal order corresponding to the different Teflon layer thicknesses. This is shown more clearly in the x-time image in FIG. 3(d), where the temperature along a single line in FIG. 3(a) is shown as a function of time. The total time for the x-time image was 8 s and the pulse length was 2.7 s. The start of the x-time image coincides with the beginning of the microwave pulse. The different times for the maximum temperature rise are easy to recognize.

Figure 4:
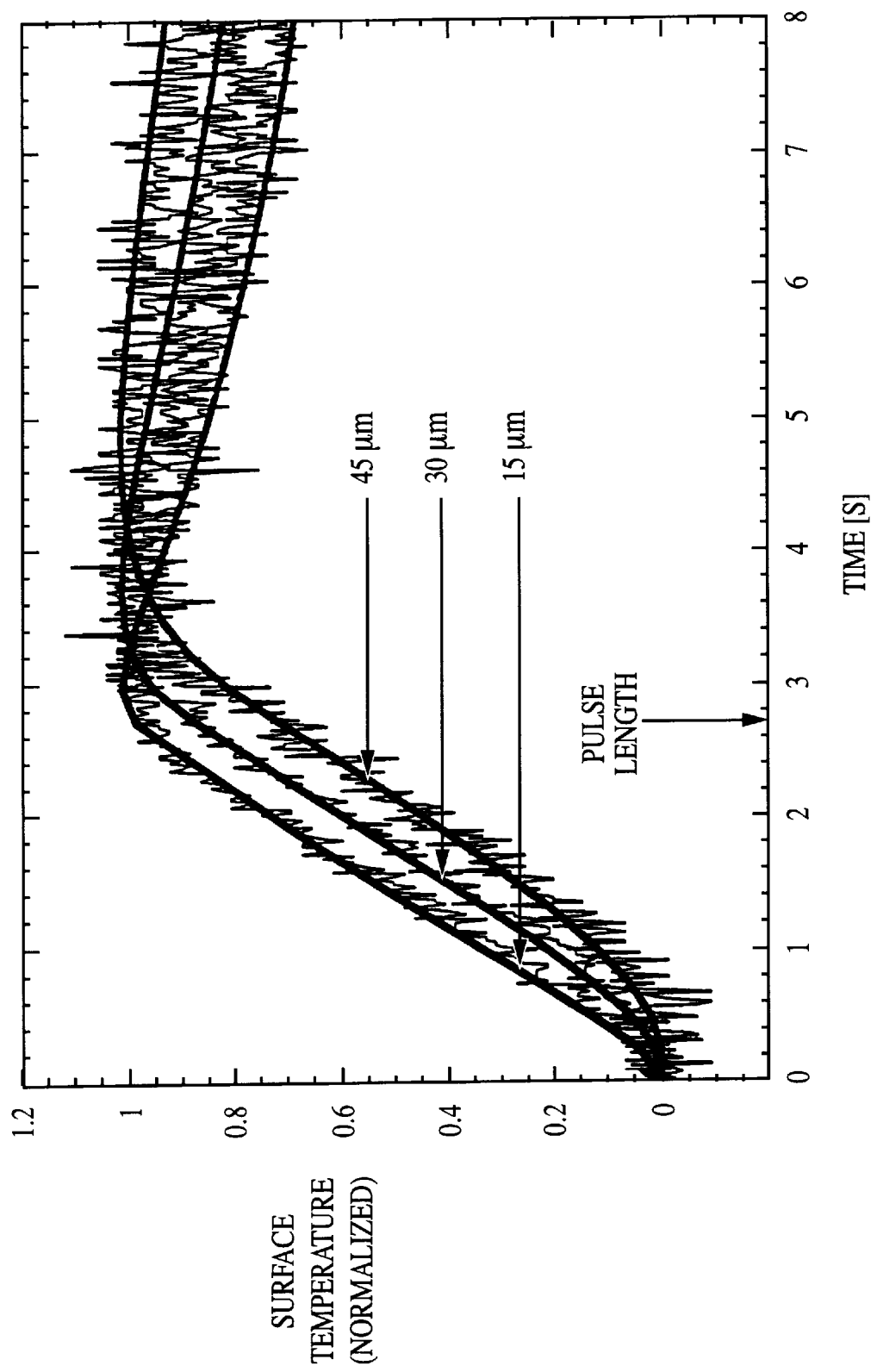
FIG. 4 illustrates plots of the surface temperature time response (normalized to the peak temperature) of the test sample for different lines taken from FIG. 3(d).

Plots of the temperature time response are shown in FIG. 4 for different lines taken from FIG. 3(d) for positions over each of the three water layers. The data has been normalized to its peak amplitude to correct for the nonuniform microwave distribution obtained, since the work was done in the near field due to power considerations. These results compare very well to theoretical calculations of the surface temperature in a one-dimensional geometry which are shown by the thick solid lines in FIG. 4.

Subsurface features in materials which can be detected using the method of the invention include boundaries/edges; nonconducting discontinuities, i.e., a dielectric loss caused by water; and conducting contaminants such as wires or graphite fibers. For the detection of fibers, a range of angles of incidence of microwaves to the sample and a range of microwave frequencies can be selected and employed to improve detectability. For example, a specific microwave frequency can cause resonant absorption of the microwaves in a conducting contaminant. The conducting contaminant is more easily detected under resonant absorption because microwave absorption is higher resulting in a greater temperature rise in the contaminant. The optimum microwave frequency to achieve resonant absorption is determined by the length and dielectric properties of the fiber and can be calculated or measured experimentally. It is also important in detecting fibers that the polarization of the microwaves match the orientation of the fiber contaminants i.e., the polarization of the microwaves must aligned (e.g., by physically orienting the microwave horn by rotation) parallel to the long axis of the contaminating fiber. There will be no excitation and, hence no detection of the contaminating fiber if the polarization is transverse to the fiber. Also, for some classes of contaminants the microwave magnetic field interaction is as important as the electric field interaction with the microwave angle of incidence and polarization impacting the magnetic field interaction as well. The sensitivity of this technique to the presence of discrete fibers provides the opportunity for development of smart materials with embedded fibers as sensors which are interrogated using the microwave thermographic technique.

The invention's use of microwave induced TRIR imaging as a quantitative nondestructive/noncontact evaluation method for characterizing subsurface defects containing water and for detecting conducting contaminants has tremendous potential. Broad classes of microwave and radio frequency absorbers should be accessible to such measurements and microwave sources should extend the area of application of thermal wave imaging using infrared detection. The analytical model for the time dependence of the surface temperature allows extraction of quantitative data including the depth of the defect. The measurements can be extended to other microwave absorbing systems and can be further developed by the selection of characteristic microwave wavelengths.

As with other infrared radiation imaging techniques, large area inspection is possible but high spatial resolution imaging can also be achieved at lower image sizes. The resolution is determined by the infrared optical system, not by the microwave wavelength; subwavelength imaging has been demonstrated to 30 $\mu$m resolution. Since the imaging process is wavelength independent with a high depth resolution, microwave photothermal measurements potentially allow spectroscopic measurements to be made even for strongly absorbing materials.

Possible applications of microwave-induced infrared imaging include:

a. detecting water in composites or beneath coatings;

b. detecting fiber breakage (impact damage), such breakage showing up as an anomaly or hot spot;

c. evaluating low observable materials for contaminants including the development of real time manufacturing process control;

d. substituting for a strain gauge when used to illuminate and detect movement in prearranged fibers attached to a structure, e.g, a bridge;

e. studying cure rates for composites;

f. providing a new approach for measurements on disordered materials as well as materials of biological and medical interest; and g. in general, for high spatial resolution imaging of microwave absorbing regions on and in a range of materials.

We claim:

1. A method for noncontact detection of electrical and magnetic property discontinuities, the discontinuities each comprising a subsurface microwave-absorbing region in a material, the method comprising the steps of:

heating directly the subsurface microwave-absorbing regions of the material with microwaves;

monitoring changes in the temperature of the surface of the material as a function of time, the changes due to the heating of the microwave-absorbing regions; and detecting the electrical and magnetic property discontinuities in the material using the changes in surface temperature.

2. The method as recited in claim 1, further comprising the step of varying the frequency of the microwaves, the varying frequency selectively exciting a molecular species in the material.

3. The method as recited in claim 1, the monitoring the surface temperature step comprising the step of monitoring the variations in the optical reflectivity of the surface of the material.

4. The method as recited in claim 1, the monitoring the surface temperature step comprising the step of monitoring the deflection of a probe beam skimming over the surface of the material.

5. The method as recited in claim 1, wherein the changes in temperature are monitored using a temperature sensing means.

6. The method as recited in claim 5, wherein the temperature sensing means comprises an infrared imaging device.

7. The method as recited in claim 6, wherein the infrared imaging device comprises a focal plane array.

8. The method as recited in claim 1, the detecting step comprising the step of detecting a dielectric loss.

9. The method as recited in claim 1, the detecting step comprising the step of detecting a boundary or edge.

10. The method as recited in claim 1, the detecting step comprising the step of detecting a nonconducting discontinuity.

11. The method as recited in claim 1, the detecting step comprising the step of detecting a conducting contaminant.

12. The method as recited in claim 11, further comprising the step of selecting an angle of polarization of the microwaves to the material, the selected angle of polarization causing the polarization of the microwaves to match the orientation of the conducting contaminant.

13. The method as recited in claim 11, further comprising the step of selecting a frequency of the microwaves, the selected frequency causing resonant absorption of the microwaves in the conducting contaminant.

14. A method for noncontact detection of an electrical property discontinuity, the discontinuity comprising a subsurface microwave-absorbing region in a material, the method comprising the steps of:

heating directly the subsurface microwave-absorbing region of the material with microwaves;

monitoring a change in the temperature of the surface of the material as a function of time, the change due to the heating of the subsurface microwave-absorbing region; and detecting the electrical property discontinuity in the material using the change in surface temperature.

15. The method as recited in claim 14, the detecting step further comprising the step of determining the depth of the electrical property discontinuity in the material.

16. The method as recited in claim 14, the detecting step comprising the step of detecting a dielectric loss.

17. A method for noncontact detection of a magnetic property discontinuity, the discontinuity comprising a subsurface microwave-absorbing region in a material, the method comprising the step of:

heating directly the subsurface microwave-absorbing region of the material with microwaves;

monitoring a change in the temperature of the surface of the material as a function of time, the change due to the heating of the subsurface microwave-absorbing region; and detecting the magnetic property discontinuity in the material using the change in surface temperature.

18. The method as recited in claim 17, the detecting step further comprising the step of determining the depth of the magnetic property discontinuity in the material.

19. The method as recited in claims 14 or 17, further comprising the step of varying the frequency of the microwaves, the varying frequency selectively exciting a molecular species in the material.

20. The method as recited in claims 14 or 17, the monitoring the surface temperature step comprising the step of monitoring the variations in the optical reflectivity of the surface of the material.

21. The method as recited in claims 14 or 17, the monitoring the surface temperature step comprising the step of monitoring the deflection of a probe beam skimming over the surface of the material.

22. The method as recited in claims 14 or 17, wherein the change in temperature is monitored using a temperature sensing means.

23. The method as recited in claim 22, wherein the temperature sensing means comprises an infrared imaging device.

24. The method as recited in claim 23, wherein the infrared imaging device comprises a focal plane array.

25. The method as recited in claims 14 or 17, the detecting step comprising the step of detecting a boundary or edge.

26. The method as recited in claims 14 or 17, the detecting step comprising the step of detecting a nonconducting discontinuity.

27. The method as recited in claims 14 or 17, the detecting step comprising the step of detecting a conducing contaminant.

28. The method as recited in claim 27, further comprising the step of selecting an angle of polarization of the microwaves to the material, the selected angle of polarization causing the polarization of the microwaves to match the orientation of the conducting contaminant.

29. The method as recited in claim 27, further comprising the step of selecting a frequency of the microwaves, the selected frequency causing resonant absorption of the microwaves in the conducting contaminant.

\* \* \* \* \*